United States Patent [19]

Takahashi et al.

[11] Patent Number: 4,638,057
[45] Date of Patent: * Jan. 20, 1987

[54] CELLULOSE ACETATE MOLDING CONTAINING ODORIFEROUS SUBSTANCE

[75] Inventors: Shigeyuki Takahashi, Himeji; Manabu Uchida; Kazuhiro Yamazaki, both of Hyogo, all of Japan

[73] Assignee: Daicel Chemical Industries, Ltd., Sakai, Japan

[*] Notice: The portion of the term of this patent subsequent to Nov. 5, 2002 has been disclaimed.

[21] Appl. No.: 706,219

[22] Filed: Feb. 27, 1985

[51] Int. Cl.$^4$ .............................................. C08B 3/06
[52] U.S. Cl. .................... 536/76; 514/781; 514/947; 239/6; 239/34; 239/60; 43/131; 536/69; 428/402
[58] Field of Search ............... 514/781, 947; 239/6, 239/34, 60; 43/131; 536/69, 76; 428/402

[56] References Cited

U.S. PATENT DOCUMENTS

| | | | |
|---|---|---|---|
| 1,899,061 | 2/1933 | Silberrad et al. | 536/76 |
| 1,993,782 | 3/1935 | Haney | 536/76 |
| 2,140,543 | 12/1938 | Northrop et al. | 536/76 |
| 2,809,192 | 10/1957 | Sloan et al. | 536/76 |
| 3,414,640 | 12/1968 | Garetto et al. | 264/140 |
| 3,785,561 | 1/1974 | Confino et al. | 239/60 |
| 4,024,334 | 5/1977 | Chandler et al. | 536/69 |
| 4,063,017 | 12/1977 | Tsao et al. | 264/13 |
| 4,228,276 | 10/1980 | Kuo et al. | 536/76 |
| 4,312,980 | 1/1982 | Motozato et al. | 536/76 |
| 4,390,691 | 6/1983 | Nishikawa et al. | 536/76 |
| 4,551,389 | 11/1985 | Ohtake et al. | 428/402 |

FOREIGN PATENT DOCUMENTS 25639 3/1981 European Pat. Off. ............. 536/76

Primary Examiner—Ronald W. Griffin
Attorney, Agent, or Firm—Flynn, Thiel, Boutell & Tanis

[57] ABSTRACT

A porous cellulose acetate molding containing an odoriferous substance is provided which is prepared by incorporating an odoriferous substance in a porous molding comprising cellulose acetate having a combined acetic acid of 50 to 58%, a pore volume of at least 0.65 cc/g and a collapsing strength of at least 10 kg. Said porous cellulose acetate may be one which is surface-saponified. Examples of the odoriferous substances include volatile substances such as insect repellents, antibacterials and mold inhibitors. Said porous cellulose acetate molding can adsorb the odoriferous substances fully without substantially changing its shape and persistently volatilize the substance for a long time.

3 Claims, 4 Drawing Figures

CELLULOSE ACETATE MOLDING CONTAINING ODORIFEROUS SUBSTANCE

BACKGROUND OF THE INVENTION

1. Field of the Invention

The present invention relates to a porous molding containing an odoriferous substance obtained by impregnating a cellulose acetate-based porous molding with at least one odoriferous substance such as an aromatizing agent or a volatile insect repellent by adsorption.

2. Description of the Prior Art

As understood from scent bags, pastilles, etc., means for stably and slowly releasing an odoriferous substance such as a perfume or a volatile insect repellent over a long period of time were devised considerably long time ago.

In recent years, proposals were made of, for example, a process for obtaining a plastic article having an aromaticity by allowing an adsorptive porous powder to adsorb an odoriferous substance, dispersing the powder in a gas-permeable plastic and molding the plastic after pelletization (Japanese Patent Publication No. 6283/1968), and a process comprising incorporating a volatile chemical in a thermoplastic elastomer comprising blocks containing polymer segments having a strong intermolecular bonding force and those having a weak intermolecular bonding force (Japanese Patent Laid-Open No. 115377/1981).

Scent bags, pastilles and the products obtained by the above processes, however, have the drawbacks that their perfume contents are as low as several to about ten %, that the persistence of their fragrance is short and that the fragrance is weak.

When imparting the aromaticity to a plastic article, restrictions are placed on the amount, kind, etc., of the aromatizing agent (perfume) added to the plastic, because it does not usually have sufficient compatibility with plastics, and is easily evaporated during molding after pelletization. In addition, it is difficult to use an easily volatile aromatizing agent.

When the thermoplastic elastomer having blocks comprising polymer segments having a strong intermolecular bonding force and those having a weak intermolecular bonding force is used as a carrier for adsorption and volatilization of a volatile chemical, these is a restriction that a choice must be made of those chemicals and diluents therefor which show an affinity for the polymer segments having a weak intermolecular bonding force but show less affinity for the polymer segments having a strong intermolecular bonding force.

The requirements for a material (carrier) for adsorbing an odoriferous substance and releasing the adsorbed odoriferous substance are as follows. Firstly, the odoriferous substance is chemically inert to the carrier. Secondly, the carrier can fully adsorb the odoriferous substance. Thirdly, the external shape of the carrier does not change substantially after adsorption of the odoriferous substance. Fourthly, the odoriferous substance is released at a moderate rate and the composition of the released component does not change appreciably with the lapse of time. The third requirement that the external shape of a carrier does not change substantially is particularly important for designing commercial products when the carrier comprises a molding.

SUMMARY OF THE INVENTION

As a result of a variety of studies, the inventors of the present invention have found that a porous molding based on cellulose acetate of a high pore volume has the property of fully adsorbing an odoriferous substance without substantially undergoing changes of its external shape and of continuously and consistently releasing the adsorbed odoriferous substance over a long period of time, and have reached the present invention.

It is an object of the present invention to provide a porous cellulose acetate molding containing an odoriferous substance, which is prepared by incorporating an odoriferous substance in a porous molding comprising cellulose acetate having a degree of acetylation of 50 to 58%, a pore volume of at least 0.65 cc/g and a collapsing strength of at least 10 kg. References to "a degree of acetylation" may be freely interchanged with "a combined acetic acid."

The cellulose acetate used in the present invention is one containing hydroxyl and acetate groups and having a degree of acetylation of from 50 to 58%. The porous molding can be formed by a solution of cellulose acetate in acetone or acetic acid, coagulating it by extrusion into a suitable coagulation bath, for example, an aqueous acetone solution or an aqueous acetic acid solution, molding the extrudate while it still exhibits plasticity, and washing the product. The porous molding can take a variety of forms, among which spherical particles are advantageous from the viewpoint of fluidity, strength, surface area, etc., and those particles which have a diameter of 0.5 to 10 mm and a sphericity of at least 0.8 can be used more advantageously. In addition, it is possible to use a molding of any desired shape, prepared by forming the above molding. The porous molding produced by this process shows a large collapsing strength in spite of its large pore volume. The porous molding which can be used in the present invention is one having a pore volume of at least 0.65 cc/g and a collapsing strength of at least 10 kg. The fact that the cellulose acetate according to the present invention has a degree of acetylation falling within the above range is thought to contribute to the features that the molding can adsorb a wide variety of aromatizing agents by virtue of a good balance between the hydroxyl groups and the acetate groups, that when the molding releases the adsorbed aromatizing agent, the composition of the released component does not change with the lapse of time even when a compounded aromatizing agent is used, and that the persistence of fragrance is good. A pore volume of below 0.65 cc/g is not practical because the amount of an odoriferous substance which can be adsorbed is low. A collapsing strength of below 10 kg is not practical because the particles undergo disintegration or the like. When spherical particles have a particle diameter of below 0.5 mm or above 10 mm, a problem of washing, etc., arises during the production, or they are difficult to handle in adsorbing an odoriferous substance.

It is also possible to use a product obtained by saponifying the outer surface of the porous molding of the present invention.

Cellulose acetate essentially shows considerable affinity for polar substances such as ester, ketone, lactone, aldehyde, or phenol, so that some kinds of perfumes or the like supported on the molding cause surface stickiness of the molding, and the surface of the molding becomes sticky or the particles of the molding stick together. These phenomena can be overcome by saponifying the outer surface of the porous molding. The saponification can be performed by immersing the porous cellulose acetate molding in an aqueous solution of an alkali, preferably sodium hydroxide, for a certain time. Although the degree of regeneration of the cellulose acetate into cellulose in this case depends on the concentration of the aqueous sodium hydroxide solution, the soaking time, etc., porous moldings of a high cellulose content, which are undesirable for use in a solid aromatizing agent aimed in the present invention, are produced when the above treatment is carried out with a high-concentration sodium hydroxide solution or for a long time. Therefore, the concentration of the aqueous sodium hydroxide solution is 0.2 to 5%, preferably 0.5 to 2%, and the soaking time is 1 to 10 minutes, preferably 2 to 5 minutes. The immersing temperature is 10° to 50° C., preferably a temperature around ordinary temperature. In order to decrease the amount of the alkali remaining after the saponification, it is necessary to wash the saponificate thoroughly, for remaining alkali directly causes the degradation of a perfume and this, in turn, causes an unbalanced aroma of a compounded perfume as well as degradation of the aroma.

When a porous cellulose acetate molding is saponified by the above method, the saponification occurs on only the surface of the molding. This fact can be affirmed by the fact that the surface appearance is improved and the average combined acetic acid can be kept at a value which corresponds to at least 90% of that before the treatment.

Examples of the odoriferous substances which can be used in the present invention include single perfumes, compounded perfumes, volatile insect repellents, volatile antibacterial agents, and volatile mold inhibitors. It is also possible to use these volatile substances after dilution with diluents.

The impregnation of a porous molding with an odoriferous substance can be performed, for example, by immersing the porous molding in the odoriferous substance or spraying it with the odoriferous substance. It is preferable from an economical viewpoint that the content of an odoriferous substance in the aromatizing agent of the present invention is 50 to 60% by weight. Further, it is apparent from the gist of the present invention that the cellulose acetate according to the present invention may include cellulose acetate butyrate, cellulose acetate propionate, etc., as well.

It is also possible that the cellulose acetate used in the present invention contains, if necessary, plasticizers, dyes, pigments, antistatic agents, antioxidants, etc.

Impregnation limits of perfume were measured on conventional products and the product of the present invention to examine their characteristics. Table 1 shows the results.

Although the composition of each product tested varies slightly and the result depends on the quality of a perfume, it can be concluded on the whole that the product of the present invention is excellent in that it has a large impregnation limit of perfume and a hard structure and shows no surface stickiness due to the perfumes and a good resistance to heat and that the conventional products have drawbacks in respect of shapes after impregnation of a perfume, that is, EVA is weak to heat and softened when the temperature is increased, the calcium silicate is easily disintegrated, and the silicate gel is easily broken.

TABLE 1

| Kind of products | Impregnation limit* |
| --- | --- |
| cellulose acetate particles | 160 g |
| saponified cellulose acetate particles | 120 g |
| calcium silicate pellets | 150 g |
| EVA pellets (VA content of 28%) | 30 g |
| silica gel spheres | 40 g |

*Note:
per 100 g of a base

PREFERRED EMBODIMENTS OF THE INVENTION

The present invention will now be described in detail with reference to examples thereof. In these examples, combined acetic acid, sphericity, pore volume, and collapsing strength were measured according to the following methods.

Combined acetic acid

About 5 g of a powdered sample was dried in a dryer at 100° to 105° C. for 2 hours and weighed accurately. 50 cc of purified acetone was added to this sample and the mixture was dissolved completely. 50 cc of a 0.2N aqueous NaOH solution and 50 cc of a 0.2N aqueous HCl solution were added thereto in sequence. The resulting solution was titrated with a 0.2N aqueous NaOH solution by using phenolphthalein as an indicator. The degree of acetylation was calculated according to the following equation:

$$\text{Combined acetic acid} = \frac{(A - B) \times F \times 1.201}{\text{weight (g) of sample}} \times 100(\%)$$

wherein
A: volume (cc) of 0.2N aqueous NaOH solution added
B: volume (cc) of 0.2N aqueous NaOH solution added in a blank test
F: factor of 0.2N aqueous NaOH solution Sphericity 20 particles were taken up at random and the largest and smallest diameters of each particle were measured with a micrometer. The sphericity was determined according to the following equation:

$$\text{sphericity} = \frac{\Sigma(\text{smallest diameter/largest diameter})}{20}$$

Pore volume

A mercury porosimeter (a product of Carlo Erba) was used. The volume of mercury intruded into the pores at a pressure in the range of 0 to 1,000 kg/cm$^2$G corresponded to a volume of pores in the range of 75 to 75,000 Å. The pore volume is represented by a volume(cc) per gram of the sample.

Collapsing strength

A Monsanto tablet hardness tester (a product of Oiwa Medical Machine Manufacturing Co., Ltd.) was used.

An average of the measured values of 10 particles was calculated.

EXAMPLE 1

Figure 1:
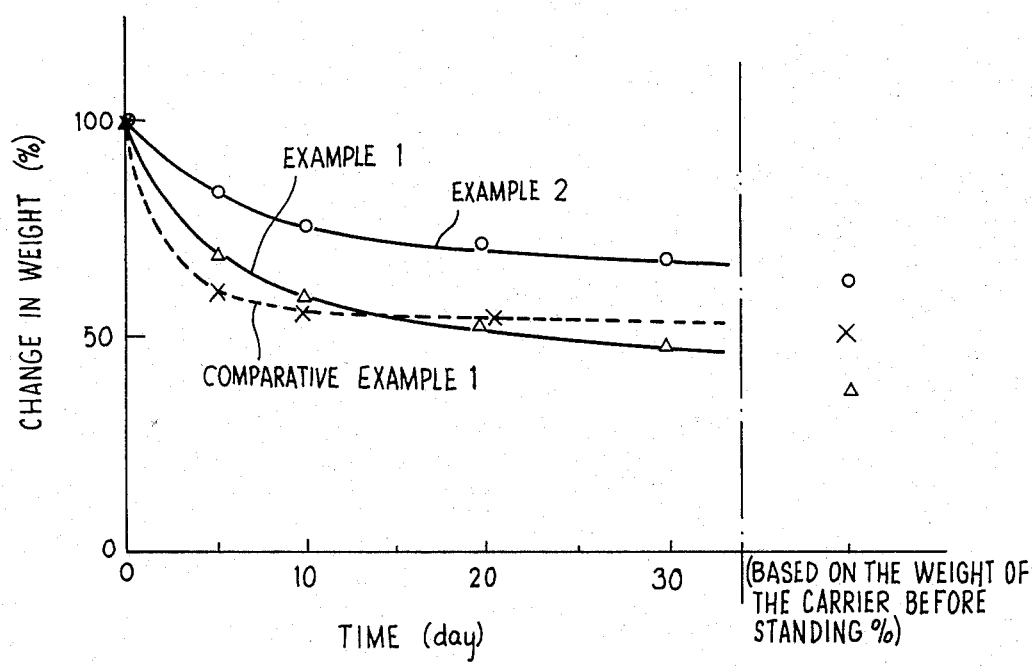
FIGS. 1 through 4 are graphs showing the changes in the amounts of odoriferous substances with the lapse of time, measured in the Examples and Comparative Examples.

Spherical cellulose acetate particles having a combined acetic acid of 54%, an average particle diameter of 4.0 mm, a sphericity of 0.9, a pore volume of 0.82 cc/g and a collapsing strength of 17 kg were immersed in a compounded Citrus perfume. The amount of the compounded perfume adsorbed after 24 hours was 164% based on the weight of the spherical porous cellulose acetate molding. The diameter of the spherical porous cellulose acetate molding did not change appreciably after adsorption. FIG. 1 shows the change in the weight of the spherical porous cellulose acetate molding containing the adsorbed perfume, obtained when it was left standing in a completely open air at the room temperature, preferably 25° to 29° C.

Said molding continued to release the aroma of the compounded Citrus perfume over a period of at least one month, and the aroma just after the initiation of the release did not differ appreciably from that after one month.

EXAMPLE 2

Spherical cellulose acetate particles having a combined acetic acid of 52%, an average particle diameter of 3.5 mm, a sphericity of 0.87, a pore volume of 0.75 cc/g, and a collapsing strength of 20 kg were immersed in the same compounded perfume as that used in Example 1 to effect adsorption under the same conditions as in Example 1. The amount of the perfume adsorbed was 57%. FIG. 1 shows the change in the weight of the spherical porous cellulose acetate molding containing the adsorbed perfume, obtained when it was left standing in the same way as in Example 1. The release characteristics were substantially the same as those in Example 1.

EXAMPLE 3

A cubic molding (pore volume of 0.80 cc/g) having a side of 35 mm formed by using the same spherical porous cellulose acetate molding as that used in Example 1 was immersed in the same odoriferous substance as that used in Example 1. The amount of the odoriferous substance adsorbed after 24 hours was 160%, based on the weight of the molding. The molding did not change appreciably in shape after the adsorption, and persistently released an aroma over a period of at least one month.

EXAMPLE 4

The same spherical porous cellulose acetate molding as that used in Example 1 was immersed in a compounded rose perfume for 24 hours. The amount of the odoriferous substance adsorbed was 158%. The molding did not change appreciably in its shape after adsorption. This molding perristently released the aroma of the compounded rose perfume over a period of at least one month. In addition, the aroma just after the initiation of the release was substantially the same as that after about one month.

COMPARATIVE EXAMPLE 1

A No.5 filter paper (a product of Toyo Filter Paper Co., Ltd.) was cut into squares of a size of 2 cm×2 cm, and these squares were immersed in the same compounded Citrus perfume as that used in Example 1 for 24 hours. The amount of the perfume adsorbed was 93% based on the weight of the filter paper squares. Three of these squares were laid upon each other and left standing in a completely open air at 25° to 29° C. FIG. 1 shows the change in the weight with the lapse of time in this case. The aroma was extremely weakened after about 10 days, and it could hardly be scented after about 15 days.

COMPARATIVE EXAMPLE 2

When substantially spherical particles (an average particle diameter of 3.5 mm) of an ethylene/vinyl acetate copolymer (vinyl acetate content of 8 mol %) were immersed in the same compounded Citrus perfume as that used in Example 1, the particles were swollen with the lapse of time to such an extent that the diameter increased 2.5-fold.

EXAMPLE 5

Figure 2:
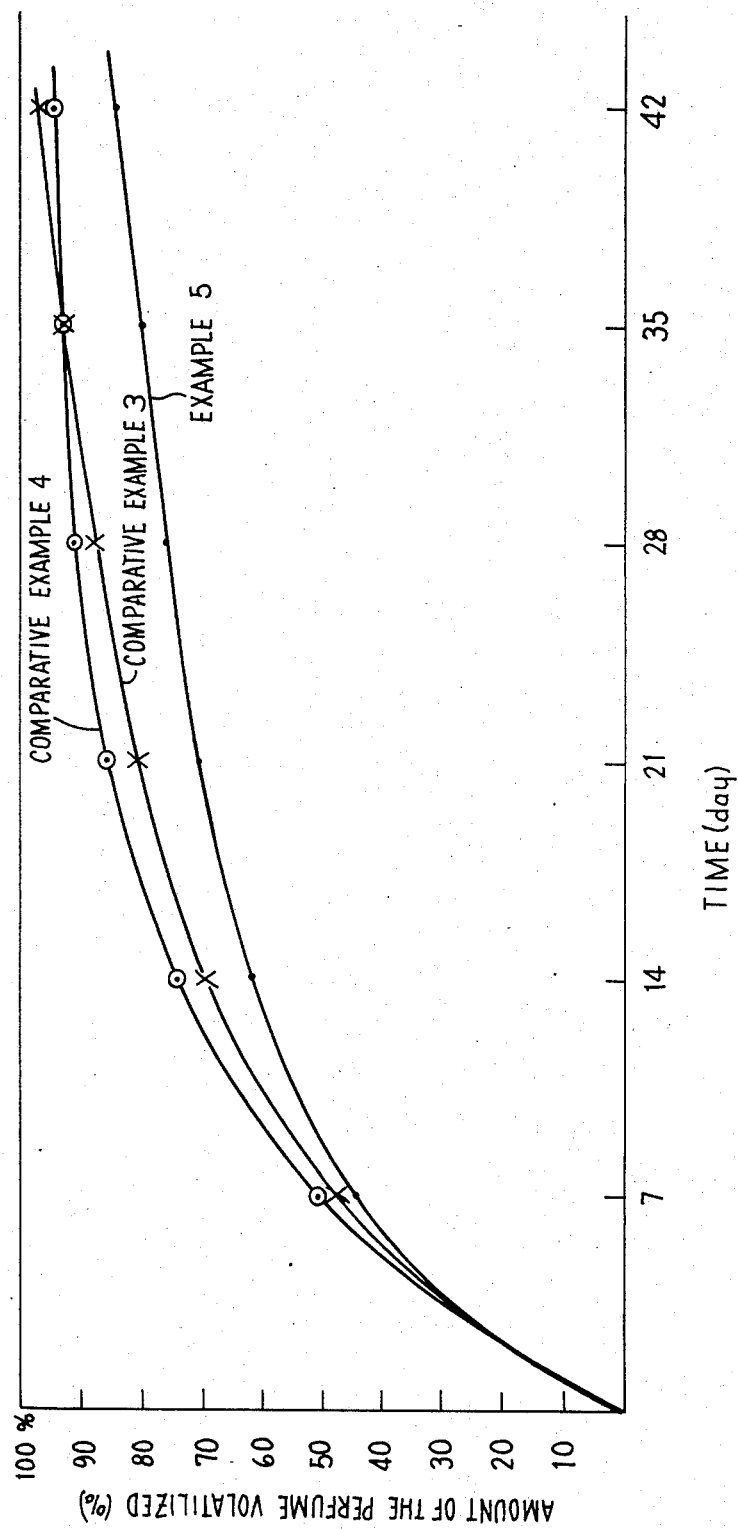

About 100 g of spherical cellulose acetate particles having a combined acetic acid of 54.5%, an average particle diameter of 3.6 mm, a sphericity of 0.87, a pore volume of 0.82 cc/g, and a collapsing strength of 20 kg were immersed in 500 cc of a 1% aqueous sodium hydroxide solution with stirring at the room temperature for 3 minutes. The particles were dewatered by a centrifuge machine washed with warm water (40° C.) for 3 hours and dried for 3 hours in a dryer at 100° to 110° C. to obtain spherical surface-saponified cellulose acetate particles. These particles had a combined acetic acid of 53.4%, an average particle diameter of 3.2 mm, a sphericity of 0.82, a pore volume of 0.75 cc/g, and a collapsing strength of 15 kg. When these particles were impregnated with 20%, based on the weight of the particles, of Lemon-pH-5526 (a product of Takasago Corporation), which based on a terpene hydrocarbon perfume, the impregnation was completed after about 10 minutes. These particles impregnated with perfume did not show surface stickiness nor adhesion among the particles when left standing in a high-temperature chamber of 80° C., thus functioning as a solid aromatizing agent. 10 g of this agent was placed and left standing in a glass Petri dish 10 cm in diameter and 1.5 cm in depth to measure the rate of volatilization at room temperature. Nine days were necessary for 50% volatilization and 45 days were necessary for 90% volatilization. This suggested an excellent effect of slow release. FIG. 2 shows the change in the amount of the perfume volatilized with the lapse of time.

COMPARATIVE EXAMPLES 3 and 4

When each of spherical calcium silicate particles having a particle diameter of 5.0 mm, a sphericity of 0.9 and a collapsing strength of 3.5 kg ( Florite R-5), a product of Tokuyama Soda Co., Ltd.) (Comparative Example 3) and EVA pellets (vinyl acetate contents of 28%, particle diameter of 3 to 4 mm) (Comparative Example 4) was impregnated with 20% of the same perfume as that used in Example 5 in the same way as in Example 5, the impregnation was completed after about 5 minutes.

The perfume within these particles was released at a rate such that 50% of the perfume initially present was released after 5 to 8 days, and all of the perfume was released after one month. These particles were fragile and easily disintegrated into powder. FIG. 2 shows the change in the amount of the perfume volatilized with the lapse of time.

EXAMPLE 6

Figure 3:
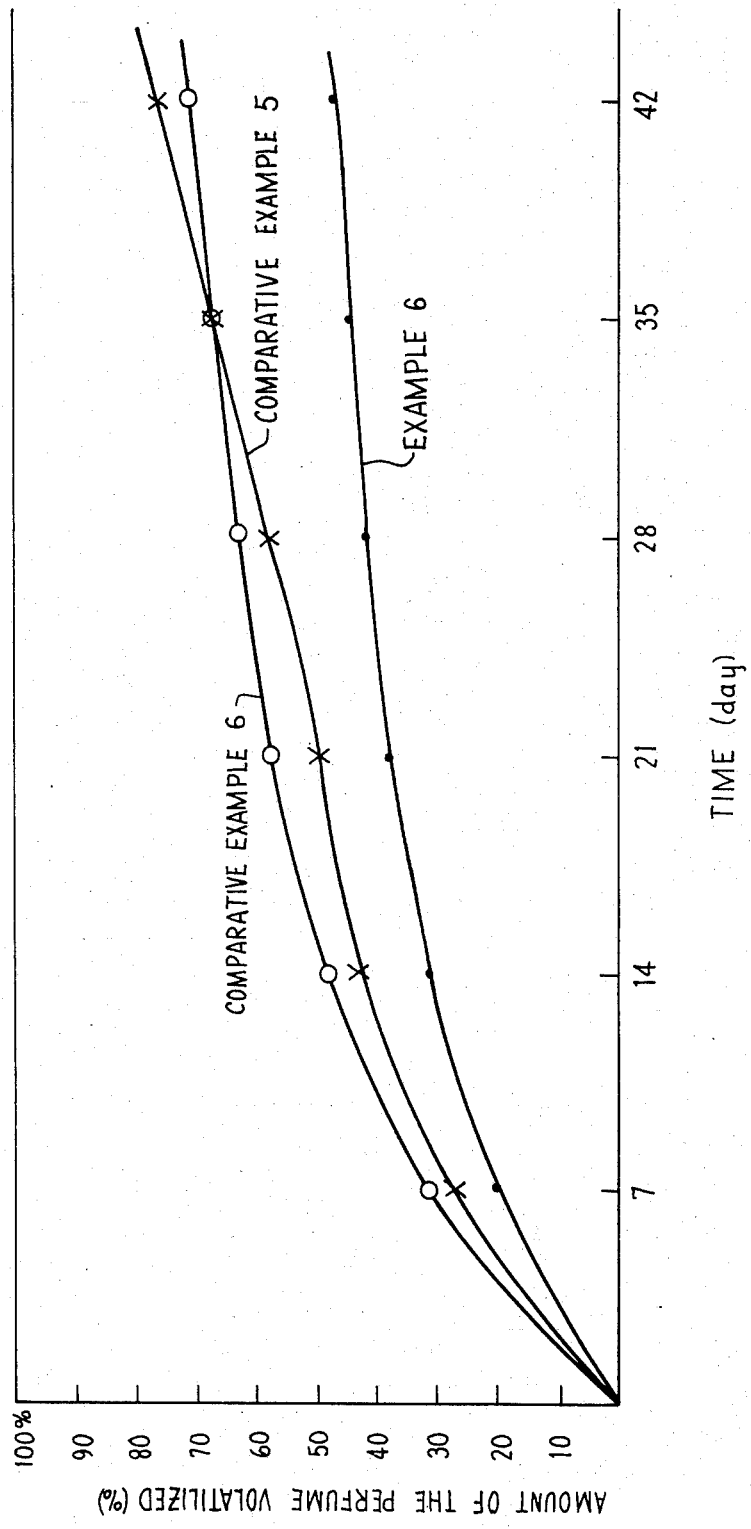

100 g of spherical cellulose acetate particles having a combined acetic acid of 55.2%, an average particle diameter of 5.3 mm, a sphericity of 0.9, a pore volume of 0.85 cc/g and a collapsing strength of 18 kg were immersed in 500 cc of a 0.5% aqueous sodium hydroxide solution with stirring at room temperature for 5 minutes and treated in the same way as in Example 5 to obtain cellulose acetate particles. The particles had a combined acetic acid of 54.5%, an average particle diameter of 5.1 mm, a sphericity of 0.85, a pore volume of 0.80 cc/g and a collapsing strength of 15 kg. When these particles were impregnated with 20%, based on the weight of the particles, of Green Apple pH-5527 (a product of Takasago Corporation), which was based on an ester perfume, the impregnation was completed after about 15 minutes. The change in the amount of the perfume volatilized with the lapse of time was measured in the same way as in Example 5. FIG. 3 shows the results. The aromatizing agent of the present invention showed an excellent effect of slow release such that 25 days were necessary for 40% release.

COMPARATIVE EXAMPLES 5 and 6

Each of the same spherical calcium silicate particles (Comparative Example 5) and EVA pellets (Comparative Example 6) as those used in Comparative Examples 3 and 4, respectively, was impregnated with 20% of the same perfume as that used in Example 6, the change in the amount of the perfume volatilized with the lapse of time was measured. FIG. 3 shows the results. 12 and 10 days were necessary for 40% release of the perfume, respectively. These rate are higher than that of Example 6.

EXAMPLE 7

Figure 4:
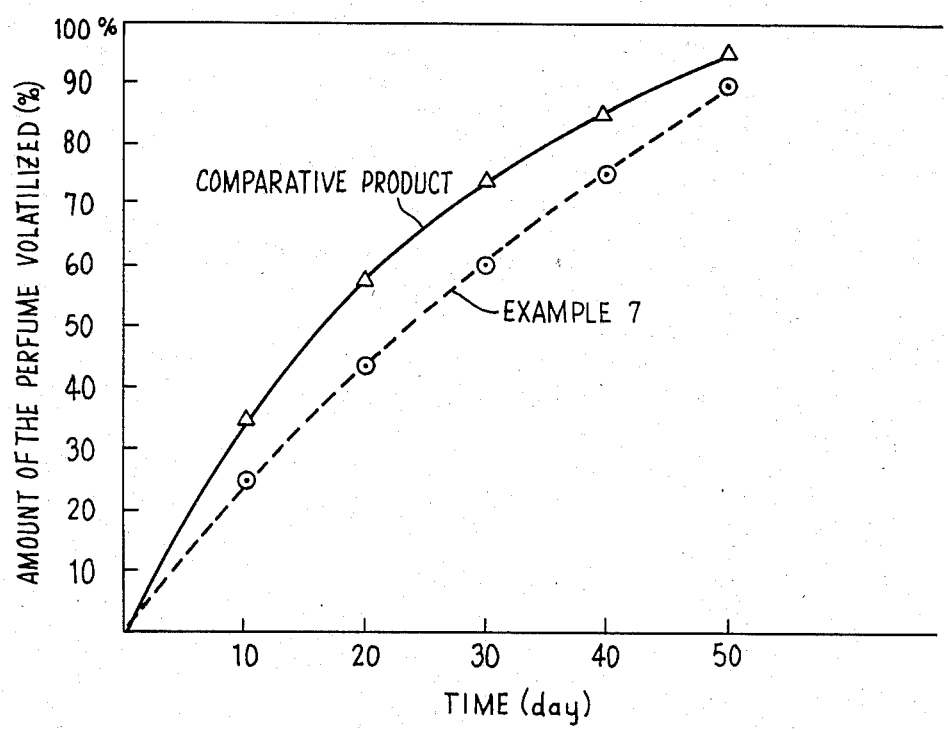

18 g of a porous plate-form molding (70 mm×70 mm×15 mm) of cellulose acetate of a combined acetic acid of 55% was immersed in 500 ml of a 0.5% aqueous sodium hydroxide solution with stirring at room temperature for 5 minutes and dehydrated, washed and dried in the same way as in Example 5. The obtained surface-saponified cellulose acetate molding had a pore volume of 0.7 cc/g and a collapsing strength of 15 kg. This molding was impregnated with 18 g of a compounded perfume Kinmokusei pH-5528 (a product of Takasago Corporation) for about 40 minutes. The molding containing the impregnated perfume did not show surface stickiness due to the perfume and maintained a satisfactory state when it was left standing at a temperature of as high as 80° C. To compare the volatility of the perfume, cuttings of a wood board for construction (70 mm×70 mm×15 mm, a product of Takasago Corporation) were impregnated with 18 g of the above compounded perfume. Both of the above aromatizing agents were set in an air duct in position to provide the same condition and air was blown into the duct at a rate of 2.8 m/sec. FIG. 4 shows the obtained results. These results also show that the aromatizing agent of the present invention show an excellent effect of slow volatility.

The embodiments of the invention in which an exclusive property or privilege is claimed are defined as follows:

1. Substantially spherical porous particles of cellulose acetate containing from about 50 to about 60% by weight of an odoriferous substance in the pores thereof, said cellulose acetate having a degree of acetylation of 50 to 58%, said particles having a pore volume of at least 0.65 cc/g, a collapsing strength of at least 10 kg, a particle size of from 0.5 to 10.0 mm and a sphericity of at least 0.8.

2. Porous particles of cellulose acetate as claimed in claim 1, wherein the surfaces of said particles have been saponified.

3. Porous particles as claimed in claim 1 wherein said odoriferous substance is a perfume.

* * * * *